United States Patent [19]

Kapp, Jr. et al.

[11] 4,205,666
[45] Jun. 3, 1980

[54] PASSIVE RANGE OF MOTION APPLIANCE

[76] Inventors: John P. Kapp, Jr., 751 Oleander Dr., Oxnard, Calif. 93030; Patricia K. Jonas, 359 Tirre St., Santa Paula, Calif. 93060

[21] Appl. No.: 888,646

[22] Filed: Mar. 21, 1978

[51] Int. Cl.² ............................................. A61F 5/00
[52] U.S. Cl. .......................................... 128/68; 128/94
[58] Field of Search ............... 128/77, 80 R, 80 G, 128/94, 169, 165, 83, 84 B; 224/28 R, 28 A, 6; 273/189 R, 189 A; 272/67

[56] References Cited

U.S. PATENT DOCUMENTS

| | | | |
|---|---|---|---|
| 705,024 | 7/1902 | Bigsby | 128/94 |
| 1,048,750 | 12/1912 | Smith | 128/94 |
| 1,664,804 | 4/1928 | Allen | 224/28 A |
| 1,790,381 | 1/1931 | Keller | 128/169 |
| 2,183,265 | 12/1939 | Maloney | 128/94 |
| 2,607,340 | 8/1952 | Anderson | 128/94 |
| 3,238,939 | 3/1966 | Stubbs | 128/169 |
| 3,512,776 | 5/1970 | Thomas | 128/165 |
| 3,536,068 | 10/1970 | Stubbs | 128/169 |
| 3,875,935 | 4/1975 | Drew | 128/94 |

FOREIGN PATENT DOCUMENTS

| | | | |
|---|---|---|---|
| 260480 | 6/1913 | Fed. Rep. of Germany | 128/94 |
| 1552131 | 11/1967 | France | 128/80 |

*Primary Examiner*—Robert W. Michell
*Assistant Examiner*—Arthur S. Rose
*Attorney, Agent, or Firm*—Matthew L. Ajeman

[57] ABSTRACT

Apparatus for use in moving a disabled human limb has a cuff arrangeable on a disabled limb, and a handle assembly attached to the cuff and engageable by an able limb of the user for permitting the able limb to manipulate the disabled limb.

9 Claims, 4 Drawing Figures

PASSIVE RANGE OF MOTION APPLIANCE

BACKGROUND OF THE INVENTION

1. Field of the Invention

This invention relates generally to orthopedic devices, and particularly to a device for permitting a person with a disabled limb, such as a paralyzed arm, to manipulate that limb in an effective manner by using an able limb, such as an able arm of the person using the appliance.

2. Description of the Prior Art

A basic difficulty encountered by persons who have suffered a paralyzation of a limb due to a stroke or other injury or disease is that the diabled limb can be moved about, whether to permit the person to obtain a more comfortable position or to exercise the limb muscles, only with great difficulty, and generally requires another person to assist the invalid in manipulating the limb.

U.S. Pat. No. 2,607,340, issued Aug. 19, 1952 to H. E. Anderson, discloses a disabled limb strap in the form of a sling which wraps around a disabled or sore foot and permits the person suffering the disability to manipulate the foot by use of one of the person's arms. More specifically, this known limb strap comprises a flexible element having a loop at one end through which the element can be folded on itself in order to form a noose which engages the foot to be moved, with the other of the ends of the flexible element being engageable by a hand of the person suffering from the disability.

Numerous devices have been proposed which strap onto the wrist or arm of a person for purposes of exercising the arm. For example, U.S. Pat. No. 3,180,641, issued Apr. 27, 1965 to W. S. Shane, discloses an exercising device for marksmen in which a sleeve is strapped onto a user's forearm. Extending from this sleeve is a pocket arranged for receiving weights which will exert the requisite force on the associated forearm. Further, U.S. Pat. No. 2,832,334, issued Apr. 29, 1958 to S. H. Whitelaw, discloses a therapeutic device for use in the manipulative treatment of joints of the human body. In particular, this latter device includes a stiff lever arm mountable on a forearm by appropriate straps, which a padded sling extending part-way around the forearm for restraining the device relative to the forearm.

U.S. Pat. Nos. 3,301,552, issued Jan. 31, 1967 to M. G. S. Ryan, and 2,287,821, issued Nov. 1, 1938 to S. G. Svensson, disclose additional examples of arm exercising devices pertinent hereto, while U.S. Pat. No. 2,287,821, issued June 30, 1942 to D. O'Donovan, sets forth a combined wrist joint and distal forearm support orthopedic device which includes a sleeve strapped onto the forearm of the user.

SUMMARY OF THE INVENTION

It is an object of the present invention to provide a passive range of motion device which permits an invalid to move a disabled limb without assistance.

It is another object of the present invention to provide a passive range of motion device which permits an invalid to move a disabled limb, such as an arm, only with an able limb, such as the other arm.

Yet another object of the present invention is to provide a passive range of motion device which permits an invalid to move a disabled limb in the opposite direction to that direction moved in a previous movement, while simultaneously permitting a resistance to be provided to certain motions of the limb in order to exercise the muscles of the disabled limb.

These and other objects are achieved according to the present invention by providing a passive range of motion device for use in moving a disabled human limb, the device having: a cuff arrangeable on a disabled limb of a person so as to be secured to the limb; and a handle assembly attached to the cuff and engageable by an able limb of a person using the apparatus for permitting the able limb to manipulate the disabled limb as desired and considered necessary.

The cuff preferably includes a body member comprising a sheet constructed from a flexible material and arrangeable on a hand and wrist of a disabled arm for conforming to the shape of the hand and wrist, with a plurality of straps being attached to the body member in such conforming shape on the hand and wrist of the disabled arm.

The body member preferably has a quadrilateral shape in plan, with two sides of the quadrilateral being substantially parallel to one another and a third side being substantially perpendicular to the two parallel sides. The fourth side of the quadrilateral has an angle other than parallel and perpendicular to the other three sides of the quadrilateral, with one of the two substantially parallel sides being longer than the other of such sides and an opening being provided in the body member adjacent the longer one of the two substantially parallel sides and to the fourth side, with this opening being arranged for receiving the thumb of a hand on which the cuff is disposed.

The handle assembly preferably includes an elongated rod having spaced end portions, with a handle being connected to the rod and spaced from the end portions, and arranged for being gripped by a hand of an able arm of a person using the apparatus. A loop is mounted on the rod adjacent one of the end portions of the rod, with this loop being arranged for receiving a forearm of the able arm having the hand gripping the handle. A connector assembly is fastened to the other of the end portions of the rod and to the body member of the cuff for attaching the rod to the cuff. Preferably, the body member is constructed from two layers of sheet material, and further comprises a reinforcing piece constructed from a shelf-supporting sheet material, such as a steel, disposed between the layers of flexible material centrally of the body member as same is viewed in plan.

In one preferred embodiment of the invention, the connector assembly comprises a snap-fastener mounted on the rod at the other of the ends thereof for removable attachment to a shackle mounted on the body member of the cuff.

In another preferred embodiment of the invention, the connector assembly comprises a substantially U-shaped bracket having a pair of codirectional, coextensive leg portions and a connecting portion joining together the leg portions. The connecting portion of the bracket is rotatably mounted on the body member of the cuff, with the leg portions being disposed receiving therebetween and being pivotally connected to the other of the ends of the rod of the handle assembly. In this manner, a close, articulated joint is made between the handle assembly and the cuff of the apparatus.

DESCRIPTION OF THE PREFERRED EMBODIMENTS

Figure 1:
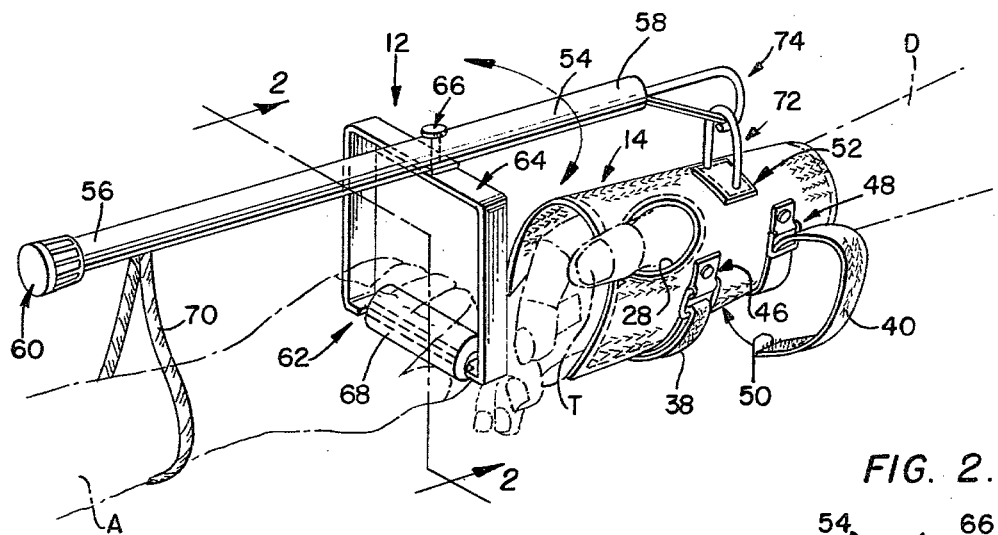
FIG. 1 is a perspective view showing a passive range of motion device according to the present invention in the process of being used to permit an able arm to manipulate a disabled arm.
Figure 2:
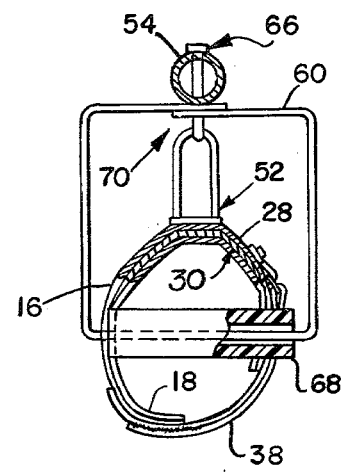
FIG. 2 is an enlarged, sectional view taken generally along the line 2—2 of FIG. 1.
Figure 3:
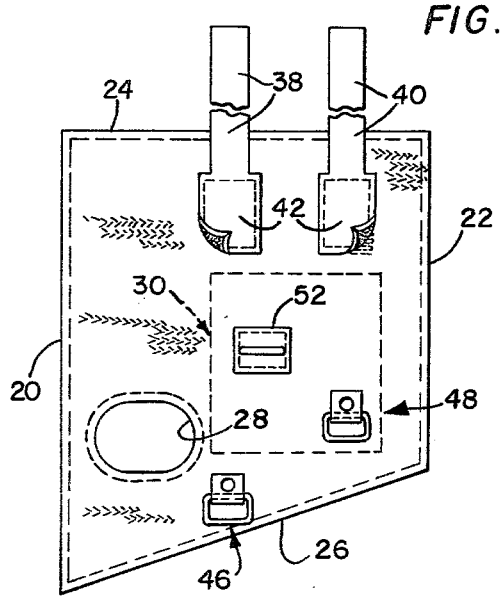
FIG. 3 is a top plan view of a cuff partially forming a passive range of motion device according to the invention.

Referring now more particularly to FIGS. 1 through 3 of the drawing, a passive range of motion device according to the present invention includes a cuff 10 arrangeable on a disabled limb D of a person, with a handle assembly 12 being attached to cuff 10 and being engageable by an able limb A of the same person for enabling the able limb to manipulate the disabled limb.

The cuff 10 includes a body member 14 comprising a pair of layers 16 and 18 constructed from flexible sheet material, such as canvas, cloth, and the like, which material is arrangeable on the hand and wrist of a disabled arm or other limb D for conforming to the shape of such hand and wrist. Body member 14 has a quadrilateral shape in plan, with two sides 20 and 22 of the quadrilateral being substantially parallel to one another, and a third side 24 of the quadrilateral being substantially perpendicular to the two substantially parallel sides 20 and 22. The fourth side 26 of the quadrilateral is disposed at an angle other than parallel and perpendicular to the sides 20, 22, and 24, with the side 20 being thus longer than the side 22. An opening 28 is formed in the body member 14 adjacent the juncture of sides 20 and 26, with this opening 28 being arranged for receiving a thumb T of the hand on which the cuff 10 is disposed.

Disposed between the layers 16 and 18 of body member 14 is a reinforcing piece 30 constructed from a sheet of self-supporting material, such as steel, and located between layers 16 and 18 centrally of body member 14 as same is seen in plan (FIG. 3). Reinforcing piece 30 has a planar web 32 and wings 34 which diverge from web 32 in opposite directions for stiffening body member 14 at the point of attachment of handle assembly 12 thereto, and for assuring that cuff 10 will tend to hold the shape thereof conforming to the hand and wrist of arm D when a force is being exerted on cuff 10 by the handle assembly 12.

The layers 16 and 18 can be attached to one another by suitable stitching, and the like, around the periphery of body member 14 and the opening 28.

Attached to body member 14 for retaining same in conforming shape on the hand and wrist of arm D is a strap arrangement 36 which comprises, as illustrated, a pair of longitudinally extending elements 38 and 40, each constructed from a flexible material such as a canvas, cloth, and the like, and having a pair of longitudinally spaced ends 42. The ends 42 are attached to the body member 14 in a suitable manner, such as by stitching. A pair of guides 46 and 48 are pivotally mounted on body member 14 for receiving the elements 38 and 40 therethrough, with a hook-fastener material 50, such as that sold under the trademark "Velcro", being provided on a surface of the elements 38 and 40 for permitting these elements to be secured to themselves after having passed through a respective one of the guides 46 and 48 so as to retain the elements 38 and 40 in their associated guides 46 and 48, and holding the cuff 10 securely on the hand and wrist of the disabled arm D. A shackle 52 is mounted on body member 14 of cuff 10 for facilitating attachment of handle assembly 12 to cuff 10 in a manner to be described below.

Handle assembly 12 includes an elongated rod 54 having spaced end portions 56 and 58, with the end portion 56 having provided thereon a conventional resilient tip 60, such as commonly found on walking canes. Connected to rod 54 at a point between and spaced from the end portions 56 and 58 is a handle 62 including a generally rectangular frame 64 attached to rod 54 by a suitable fastener 66, and provided with a generally cylindrical grip 68 arranged for being gripped by a hand of an able arm or limb A of a person using the apparatus according to the invention. A loop 70 is mounted on rod 54 in a suitable manner and disposed adjacent end portion 56 of rod 54, and is arranged for receiving a forearm of the able limb A so as to hold rod 54 in general alignment with the forearm of limb A. A connector assembly 72 is fastened to end portion 58 of rod 54 and to the body member 14 of cuff 10 for attaching rod 54 to the cuff 10. This connector assembly 72 includes a conventional snap-fastener 74 affixed to the end portion 58 of rod 54 and removably attached to shackle 52 of body member 14 for forming an articulated, releasible connection between rod 54 and body member 14.

In operation, with reference to FIG. 1, cuff 10 is strapped onto the hand and wrist of a disabled arm or other limb D by use of the flexible straps or elements 38 and 40. More specifically, the ends 44 of elements 38 and 40 are brought through the eyes or guides 46 and 48, respectively, and are brought back on themselves so that the hook-fastener material 50 portions of elements 38 and 40 are brought into engagement in order to secure the elements 38 and 40 to themselves and to their associated guides 46 and 48. In this fashion, the cuff 10 will be secured on the hand and wrist portion of a disabled arm, with the thumb T extending through the opening 28. Now the user can place the able arm in the illustrated manner with the hand thereof engaging the grip 68 of handle 62, and the forearm and/or wrist being disposed in the loop 70 so as to keep the rod 54 in general alignment with the forearm/wrist and hand of the able limb A. Thus arranged, the able limb A can be used to manipulate the disabled limb D as suitable and desired, including movement of the limb in the opposite direction from an initial movement, all the while maintaining a resistance on the limb by use of the able limb in order to exercise the muscles of the disabled limb D.

Figure 4:
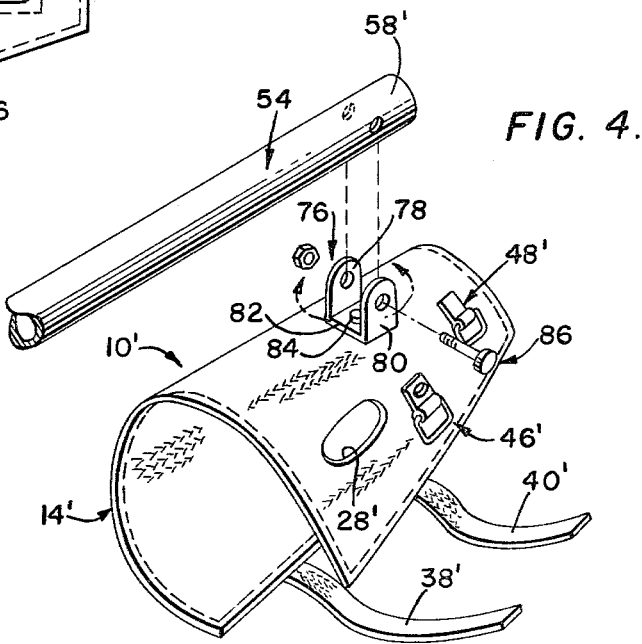
FIG. 4 is a fragmentary, exploded perspective view showing a second embodiment of the present invention.

Referring now more particularly to FIG. 4 of the drawing, a modified embodiment of the present invention is illustrated wherein the like elements to the invention illustrated in FIGS. 1 through 3 are given the same reference numerals accompanied by a prime. In this embodiment of the invention, the connector assembly 72' includes a substantially U-shaped bracket 76 having a pair of codirectional, coextensive leg portions 78 and 80, and a connecting portion 82 joining together leg portions 78 and 80. Connecting portion 82 is rotatably mounted on the body member 14' of cuff 10' in a suitable manner, such as by the use of a headed pin 84. Opposed apertures are provided in leg portions 78, 80 and in end portion 58' of rod 54' for receiving the shank of the bolt of a bolt and nut assembly 86, which assembly 86 pivotally mounts the rod 54' onto the bracket 76.

It will be appreciated that while the use of bracket 76 permits a closer and more rigid connection of rod 54' to body member 14' than is obtained for rod 54 and body member 14 of the embodiment of the invention seen in FIGS. 1 through 3, the operation of the embodiment of the invention illustrated in FIG. 4 is exactly the same as that described above for the first embodiment of the invention.

As can be readily understood from the above description and from the drawing, a passive range of motion device according to the present invention permits an invalid to move a disabled limb without assistance, with the apparatus according to the invention capable of being put on, used, and taken off of the user's person without the necessity of another person assisting the user. The entire unit weighs less than two pounds complete, so as not to add excessive weight to the user's limbs.

It is to be understood that the above description of the present invention is capable of various changes, modifications, and adaptions, and such are intended to be included within the meaning and range of equivalents of the following claims.

We claim:

1. Apparatus for use in moving a disabled human limb, comprising, in combination:
(A) a cuff arrangeable on a disabled limb of a person, the cuff including, in combination:
   (1) a body member comprising a sheet constructed from a flexible material and arrangeable on a hand and wrist of a disabled arm for conforming to the shape of the hand and wrist; and
   (2) strap means attached to the body member for retaining the body member in conforming shape on the hand and wrist of the disabled arm, the disabled arm being the disabled limb,
(B) rigid handle means attached to the cuff and engageable by an able limb separate from and not attached to the disabled limb of a person using the apparatus, for using the able limb to manipulate the disabled limb, the handle means including, in combination:
   (1) a rigid, elongated rod having spaced end portions;
   (2) a handle connected to the rod between and spaced from the end portions, the handle being arranged for being gripped by a hand of an able arm of a person using the apparatus; and
   (3) a loop mounted on the rod adjacent one of the end portions of the rod and arranged for receiving the forearm of the able arm; and
(C) means for inelastically connecting said cuff to the other of the end portions of said rod.

2. Apparatus as defined in claim 1, wherein the strap means comprises, in combination:
(a) at least two elongated elements each constructed from a flexible material and having first and second spaced ends, with the first one of the ends being attached to the body member;
(b) a pair of guides mounted on the body member at points spaced from the first of the ends of the elements for receiving an associated one of the elements; and
(c) fastener means provided on each of the elements for removably securing the element to itself and retaining the element in the respective one of the guides.

3. Apparatus as defined in claim 2, wherein the sheet forming the body member of the cuff has a quadrilateral shape in plan, with two sides of the quadrilateral being substantially parallel to one another, a third side of the quadrilateral being substantially perpendicular to the two substantially parallel sides, and the fourth side of the quadrilateral being at an angle other than parallel and perpendicular to the other three sides, one of the two substantially parallel sides being longer than the other of such sides, and an opening being provided in the body member adjacent the juncture of the longer of the two substantially parallel sides and the fourth side, the opening being arranged for receiving a thumb of the hand on which the cuff is disposed.

4. Apparatus as defined in claim 3, wherein the body member is constructed from two layers of sheet material, and further comprises a reinforcing piece constructed from a self-supporting sheet material disposed between the layers centrally of the body member as seen in plan, the reinforcing piece having a substantially planar web and a pair of wings diverging from the web for stiffening the body member at a point of attachment of the body member to the handle means.

5. Apparatus as defined in claim 1, wherein the connector means comprises, in combination:
(a) a shackle mounted on the cuff; and
(b) a snap-fastener attachment affixed to the other of the end portions of the rod and removably attached to the shackle.

6. Apparatus as defined in claim 1, wherein the connector means comprises a U-shaped bracket having a pair of codirectional, coextensive leg portions and a connecting portion joining together the leg portions, the connecting portion being rotatably mounted on the cuff, and the leg portions receiving therebetween and pivotally connected to the other of the end portions of the rod.

7. Apparatus for use in moving a disabled human limb, comprising, in combination:
(A) a cuff arrangeable on a disabled limb of a person; and
(B) handle means attached to to the cuff and engageable by an able limb of a person using the apparatus for using the able limb to manipulate the disabled limb, the cuff including, in combination:
   (1) a body member comprising a sheet constructed from a flexible material and arrangeable on a hand and wrist of a disabled arm for conforming to the shape of the hand and wrist; and
   (2) strap means attached to the body member for retaining the body member in conforming shape on the hand and wrist of the disabled arm, the disabled arm being the disabled limb, the strap means comprising, in combination:
      (a) at least two elongated elements each construted from a flexible material and having first and second spaced ends, with the first of the ends being attached to the body member;
      (b) a pair of guides mounted on the body member at points spaced from the first of the ends of the elements for receiving an associated one of the elements; and
      (c) fastener means provided on each of the elements for removably securing to itself and retaining the element in the respective one of the guides, the sheet forming the body member of the cuff having a quadrilateral shape in plan, with two sides of the quadrilateral being substantially parallel to one another, a third side of the quadrilateral being substantially perpendicular to the two substantially parallel sides, and the fourth side of the quadrilateral being at an angle other than parallel and perpendicular to the other three sides, one of the two substantially parallel sides being longer than the other of such sides, and an opening being provided in the body member adjacent the juncture of the longer of the two substantially parallel sides and the fourth side, the opening being arranged for receiving a thumb of the hand on which the cuff is disposed, the body member being constructed from two layers of sheet material, and further comprising a reinforcing piece constructed from a self-supporting sheet material disposed between the layers centrally of the body member as seen in plan, the reinforcing piece having a substantially planar web and a pair of wings diverging from the web for stiffening the body member at a point of attachment of the body member to the handle means, and the handle means including, in combination:
(3) an elongated rod having spaced end portions;
(4) a handle connected to the rod between and spaced from the end portions, the handle being arranged for being gripped by a hand of an able arm of a person using the apparatus;
(5) a loop mounted on the rod adjacent one of the end portions of the rod and arranged for receiving the forearm of the able arm; and
(6) connector means fastened to the other of the end portions of the rod and to the body member of the cuff for attaching the rod to the cuff.

8. Apparatus as defined in claim 7, wherein the connector means comprises, in combination:
(d) a shackle mounted on the body member of the cuff; and
(e) a snap-fastener attachment affixed to the other of the end portions of the rod and removably attached to the shackle.

9. Apparatus as defined in claim 7, wherein the connector means comprises a U-shaped bracket having a pair of codirectional, coextensive leg portions and a connecting portion joining together the leg portions, the connecting portion being rotatably mounted on the body member of the cuff, and the leg portions receiving therebetween and pivotally connected to the other of the end portions of the rod.

* * * * *